United States Patent
Matsutani

(10) Patent No.: US 11,410,312 B2
(45) Date of Patent: *Aug. 9, 2022

(54) DYNAMIC ANALYSIS SYSTEM

(71) Applicant: KONICA MINOLTA, INC., Tokyo (JP)

(72) Inventor: Noritsugu Matsutani, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/015,951

(22) Filed: Sep. 9, 2020

(65) Prior Publication Data

US 2020/0410684 A1 Dec. 31, 2020

Related U.S. Application Data

(63) Continuation of application No. 16/706,144, filed on Dec. 6, 2019, now Pat. No. 10,810,741, which is a (Continued)

(30) Foreign Application Priority Data

Mar. 10, 2017 (JP) .............................. JP2017-045532

(51) Int. Cl.
*G06T 7/00* (2017.01)
*A61B 6/00* (2006.01)
*G06T 7/38* (2017.01)

(52) U.S. Cl.
CPC ............ *G06T 7/0016* (2013.01); *A61B 6/463* (2013.01); *A61B 6/486* (2013.01); *A61B 6/50* (2013.01);
(Continued)

(58) Field of Classification Search
CPC ... G06T 7/0012; G06T 7/0014; G06T 7/0016; G06T 7/20; G06T 7/246; G06T 7/248;
(Continued)

(56) References Cited

U.S. PATENT DOCUMENTS

| 10,540,767 B2 | 1/2020 | Masutani | G06T 7/38 |
| 10,810,741 B2* | 10/2020 | Matsutani | G06T 7/0016 |
| 2015/0254852 A1 | 9/2015 | Yamato et al. | A61B 6/5288 |

FOREIGN PATENT DOCUMENTS

| JP | 2008-188164 A | 8/2008 | A61B 6/00 |
| WO | WO 2009/093693 A1 | 7/2009 | G06T 7/00 |
| WO | WO 2014/054379 A1 | 4/2014 | A61B 6/00 |

OTHER PUBLICATIONS

Japanese Office Action dated Jun. 8, 2020 based on JP2017-045532.

* cited by examiner

*Primary Examiner* — Andrew W Johns
(74) *Attorney, Agent, or Firm* — Cozen O'Connor

(57) ABSTRACT

A dynamic analysis system includes a hardware processor and an output device. The hardware processor obtains a cycle of temporal change in a feature amount relevant to a function to be diagnosed from each of dynamic images obtained by imaging of a dynamic state of a living body with radiation. The hardware processor further adjusts the obtained cycle, thereby generating a plurality of cycle-adjusted data having cycles of the temporal change in the feature amount being equal to one another. The hardware processor further generates difference information at each phase in the plurality of cycle-adjusted data. The output device outputs the difference information.

20 Claims, 8 Drawing Sheets

Related U.S. Application Data continuation of application No. 15/915,801, filed on Mar. 8, 2018, now Pat. No. 10,540,767.

(52) U.S. Cl.
CPC .............. *A61B 6/503* (2013.01); *A61B 6/507* (2013.01); *A61B 6/5217* (2013.01); *A61B 6/5235* (2013.01); *A61B 6/5288* (2013.01); *G06T 7/38* (2017.01); *A61B 6/468* (2013.01); *G06T 2207/10016* (2013.01); *G06T 2207/10116* (2013.01); *G06T 2207/30061* (2013.01)

(58) Field of Classification Search
CPC .. G06T 7/30; G06T 7/33; G06T 7/337; G06T 7/38; G06T 7/97; G06T 2207/20224; G06T 2207/30061; A61B 6/486; A61B 6/50; A61B 6/507
See application file for complete search history.

FIG.5
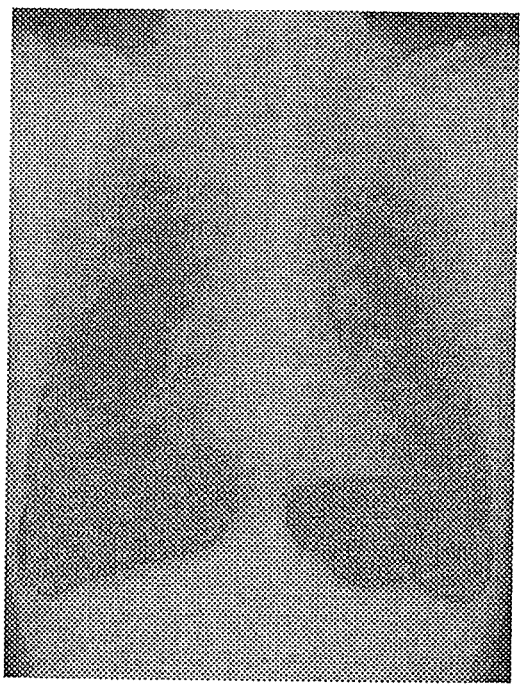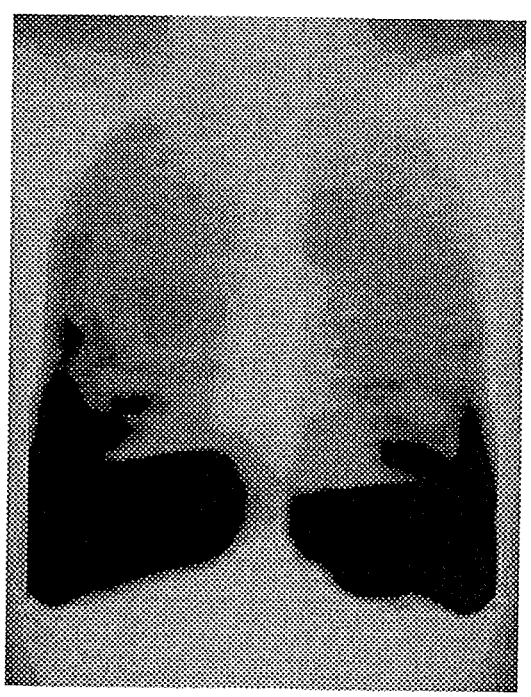
:DIFFERENCE⟨+⟩    :DIFFERENCE⟨-⟩

———:CURRENT ----:PAST ▓:DIFFERENCE⟨+⟩ ■:DIFFERENCE⟨−⟩

DYNAMIC ANALYSIS SYSTEM

RELATED APPLICATIONS

This application is a continuation of U.S. patent application Ser. No. 16/706,144 filed Dec. 6, 2019 which is a continuation of U.S. patent application Ser. No. 15/915,801 filed Mar. 8, 2018, which claims priority of Japanese application no. 2017-045532 filed Mar. 10, 2017, the entire content of all of which are hereby incorporated by reference.

BACKGROUND

1. Technological Field

This invention relates to a dynamic analysis system.

2. Description of the Related Art

When dynamic images obtained by imaging of a cyclic dynamic state of a subject are compared with one another for interpretation, there may be difference in cycle of the dynamic state between the dynamic images, which leads to inappropriate comparison and evaluation.

There is described, for example, in WO 2014/054379 A1, a technique of synchronizing cyclic changes of a base moving image and a reference moving image to be compared with the base moving image at a particular phase in each cycle of the reference moving image and displaying these two moving images.

However, even if cycles of dynamic images are matched with one another and these dynamic images are displayed simultaneously as described in WO 2014/054379 A1, it is difficult to intuitively note their difference.

SUMMARY

Objects of the invention include readily understanding difference between dynamic images that are compared with one another.

In order to achieve at least one of the objects, according to an aspect of the invention, there is provided a dynamic analysis system including: a hardware processor that: obtains a cycle of temporal change in a feature amount relevant to a function to be diagnosed from each of dynamic images obtained by imaging of a dynamic state of a living body with radiation; adjusts the obtained cycle, thereby generating a plurality of cycle-adjusted data having cycles of the temporal change in the feature amount being equal to one another; and generates difference information at each phase in the plurality of cycle-adjusted data; and an output device that outputs the difference information.

According to another aspect of the invention, there is provided a dynamic analysis system including: a hardware processor that: obtains a cycle of temporal change in a feature amount relevant to a function to be diagnosed from each of analysis result images of respective dynamic images obtained by imaging of a dynamic state of a living body with radiation, wherein the analysis result images show results of dynamic analysis of the respective dynamic images on a pixel basis or a block basis, the block being constituted of a plurality of pixels; adjusts the obtained cycle, thereby generating a plurality of cycle-adjusted data having cycles of the temporal change in the feature amount being equal to one another; and generates difference information at each phase in the plurality of cycle-adjusted data; and an output device that outputs the difference information.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the invention, wherein:

FIG. 5 shows a difference image (moving image) displayed in Step S16 in FIG. 3;

DETAILED DESCRIPTION OF EMBODIMENTS

Hereinafter, one or more embodiments of the invention will be described in detail with reference to the drawings. However, the scope of the invention is not limited to the disclosed embodiments.

First Embodiment

[Configuration of Dynamic Analysis System 100]

First, the configuration of a first embodiment is described.

Figure 1:
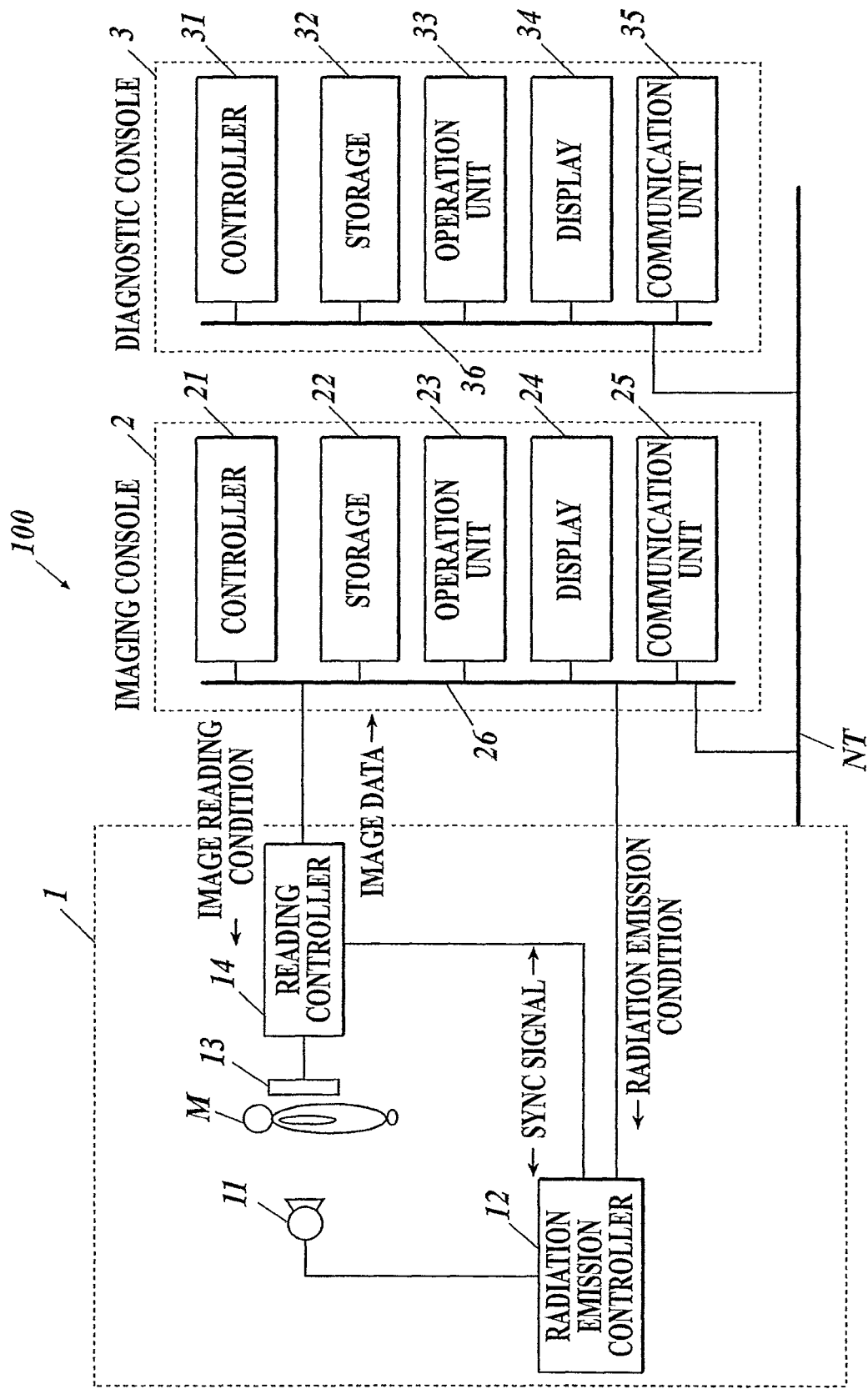
FIG. 1 shows the overall configuration of a dynamic analysis system according to embodiments of the invention.

FIG. 1 shows the overall configuration of a dynamic analysis system 100 according to the first embodiment.

As shown in FIG. 1, the dynamic analysis system 100 includes: an imager 1; an imaging console 2 connected with the imager 1 via a communication cable or the like; and a diagnostic console 3 connected with the imaging console 2 via a communication network NT, such as a LAN (Local Area Network). These apparatuses of the dynamic analysis system 100 are in conformity with DICOM (Digital Image and Communications in Medicine) standard and communicate with one another in conformity with DICOM.

[Configuration of Imager 1]

The imager 1 is an imager that images a cyclic dynamic state. Examples of the cyclic dynamic state include: change in shape of the lung fields by expansion and contraction of the lung fields with breathing; and pulsation of the heart. Dynamic imaging (kinetic imaging) is performed by repeatedly emitting pulsed radiation, such as pulsed X-rays, to a subject at predetermined time intervals (pulse emission) or continuously emitting radiation without a break to a subject at a low dose rate (continuous emission), thereby obtaining a plurality of images showing the dynamic state of the subject. A series of images obtained by dynamic imaging is called a dynamic image. Images constituting a dynamic image are called frame images. In the embodiments described hereinafter, dynamic imaging of a chest is performed by pulse emission as an example.

A radiation source 11 is disposed to face a radiation detector 13 with a subject M (examinee) interposed therebetween, and emits radiation (X-rays) to the subject M under the control of a radiation emission controller 12.

The radiation emission controller 12 is connected with the imaging console 2, and controls the radiation source 11 on the basis of radiation emission conditions input from the imaging console 2 so as to perform imaging with radiation (radiation imaging). The radiation emission conditions input from the imaging console 2 include a pulse rate, a pulse width, a pulse interval, the number of frames (frame images) to be taken by one imaging, a value of current of an X-ray tube, a value of voltage of the X-ray tube, and a type of added filter. The pulse rate is the number of times radiation is emitted per second, and matches the frame rate described below. The pulse width is duration of radiation emission per time. The pulse interval is a period of time from the start of one radiation emission to the start of the next radiation emission, and matches the frame interval described below.

The radiation detector 13 is constituted of a semiconductor image sensor, such as an FPD. The FPD is constituted of detection elements (pixels) arranged at predetermined points on a substrate, such as a glass substrate, in a matrix. The detection elements detect radiation (intensity of radiation) that has been emitted from the radiation source 11 and passed through at least the subject M, convert the detected radiation into electric signals, and accumulate the electric signals therein. The pixels are provided with switches, such as TFTs (Thin Film Transistors). There are an indirect conversion type FPD that converts X-rays into electric signals with photoelectric conversion element(s) via scintillator(s) and a direct conversion type FPD that directly converts X-rays into electric signals. Either of them can be used.

The radiation detector 13 is disposed to face the radiation source 11 with the subject M interposed therebetween.

A reading controller 14 is connected with the imaging console 2. The reading controller 14 controls the switches of the pixels of the radiation detector 13 on the basis of image reading conditions input from the imaging console 2 to switch the pixels to read the electric signals accumulated in the pixels, thereby reading the electric signals accumulated in the radiation detector 13 and obtaining image data. This image data is a frame image(s). The reading controller 14 outputs the obtained frame images to the imaging console 2. The image reading conditions include a frame rate, a frame interval, a pixel size, and an image size (matrix size). The frame rate is the number of frame images to be obtained per second, and matches the pulse rate described above. The frame interval is a period of time from the start of one frame image obtaining action to the start of the next frame image obtaining action, and matches the pulse interval described above.

The radiation emission controller 12 and the reading controller 14 are connected to one another, and exchange sync signals so as to synchronize radiation emission actions with image reading actions.

[Configuration of Imaging Console 2]

The imaging console 2 outputs the radiation emission conditions and the image reading conditions to the imager 1 so as to control the radiation imaging and the radiation image reading actions performed by the imager 1, and also displays the dynamic image obtained by the imager 1 so that a radiographer, such as a radiologist, can check if positioning has no problem, and also can determine if the dynamic image is suitable for diagnosis.

The imaging console 2 includes, as shown in FIG. 1, a controller 21, a storage 22, an operation unit 23, a display 24 and a communication unit 25. These units or the like are connected to one another via a bus 26.

The controller 21 includes a CPU (Central Processing Unit) and a RAM (Random Access Memory). The CPU of the controller 21 reads a system program and various process programs stored in the storage 22 in response to operations with the operation unit 23, opens the read programs in the RAM, and performs various processes, such as the below-described imaging control process, in accordance with the opened programs, thereby performing concentrated control of actions of the units or the like of the imaging console 2 and the radiation emission actions and the reading actions of the imager 1.

The storage 22 is constituted of a nonvolatile semiconductor memory, a hard disk or the like. The storage 22 stores therein various programs to be executed by the controller 21, parameters necessary to perform processes of the programs, data, such as process results, and so forth. For example, the storage 22 stores therein a program for the imaging control process shown in FIG. 2. The storage 22 also stores therein the radiation emission conditions and the image reading conditions for respective imaging sites to be examined (here, the chest). The programs are stored in the form of computer readable program code, and the controller 21 acts in accordance with the program code.

The operation unit 23 includes: a keyboard including cursor keys, number input keys and various function keys; and a pointing device, such as a mouse, and outputs, to the controller 21, command signals input by key operations on the keyboard or by mouse operations. The operation unit 23 may have a touchscreen on the display screen of the display 24. In this case, the operation unit 23 outputs command signals input via the touchscreen to the controller 21.

The display 24 is constituted of a monitor, such as an LCD (Liquid Crystal Display) or a CRT (Cathode Ray Tube), and displays thereon input commands from the operation unit 23, data and so forth in accordance with commands of display signals input from the controller 21.

The communication unit 25 includes a LAN adapter, a modem and a TA (Terminal Adapter), and controls data exchange with apparatuses connected to the communication network NT.

[Configuration of Diagnostic Console 3]

The diagnostic control 3 is an apparatus that obtains the dynamic image from the imaging console 2, and displays the obtained dynamic image and/or the analysis result of the dynamic image to help a doctor(s) make a diagnosis.

The diagnostic console 3 includes, as shown in FIG. 1, a controller 31, a storage 32, an operation unit 33, a display 34 and a communication unit 35. These units or the like are connected to one another via a bus 36.

The controller 31 includes a CPU (hardware processor) and a RAM. The CPU of the controller 31 reads a system program and various process programs stored in the storage 32 in response to operations with the operation unit 33, opens the read programs in the RAM, and performs various processes, such as the below-described difference display process A, in accordance with the opened programs, thereby performing concentrated control of actions of the units or the like of the diagnostic console 3.

The storage 32 is constituted of a nonvolatile semiconductor memory, a hard disk or the like. The storage 32 stores therein various programs, including a program for the difference display process A, to be executed by the controller 31, parameters necessary to perform processes of the programs, data, such as process results, and so forth. The programs are stored in the form of computer readable program code, and the controller 31 acts in accordance with the program code.

The storage 32 stores therein the dynamic image, which has been taken in the past, correlated with patient information (e.g. patient ID, name, height, weight, age, sex, etc.) and examination information (e.g. examination ID, examination date, site to be examined (here, the chest), type of function to be diagnosed (e.g. ventilation, perfusion, diaphragm, etc.), etc.).

The operation unit 33 includes: a keyboard including cursor keys, number input keys and various function keys; and a pointing device, such as a mouse, and outputs, to the controller 31, command signals input by key operations on the keyboard or by mouse operations. The operation unit 33 may have a touchscreen on the display screen of the display 34. In this case, the operation unit 33 outputs command signals input via the touchscreen to the controller 31.

The display 34 is constituted of a monitor, such as an LCD or a CRT, and performs various types of display in accordance with commands of display signals input from the controller 31.

The communication unit 35 includes a LAN adapter, a modem and a TA, and controls data exchange with apparatuses connected to the communication network NT.

[Actions of Dynamic Analysis System 100]

Next, actions of the dynamic analysis system 100 according to this embodiment are described.

[Actions of Imager 1 and Imaging Console 2]

First, imaging actions that are performed by the imager 1 and the imaging console 2 are described.

Figure 2:
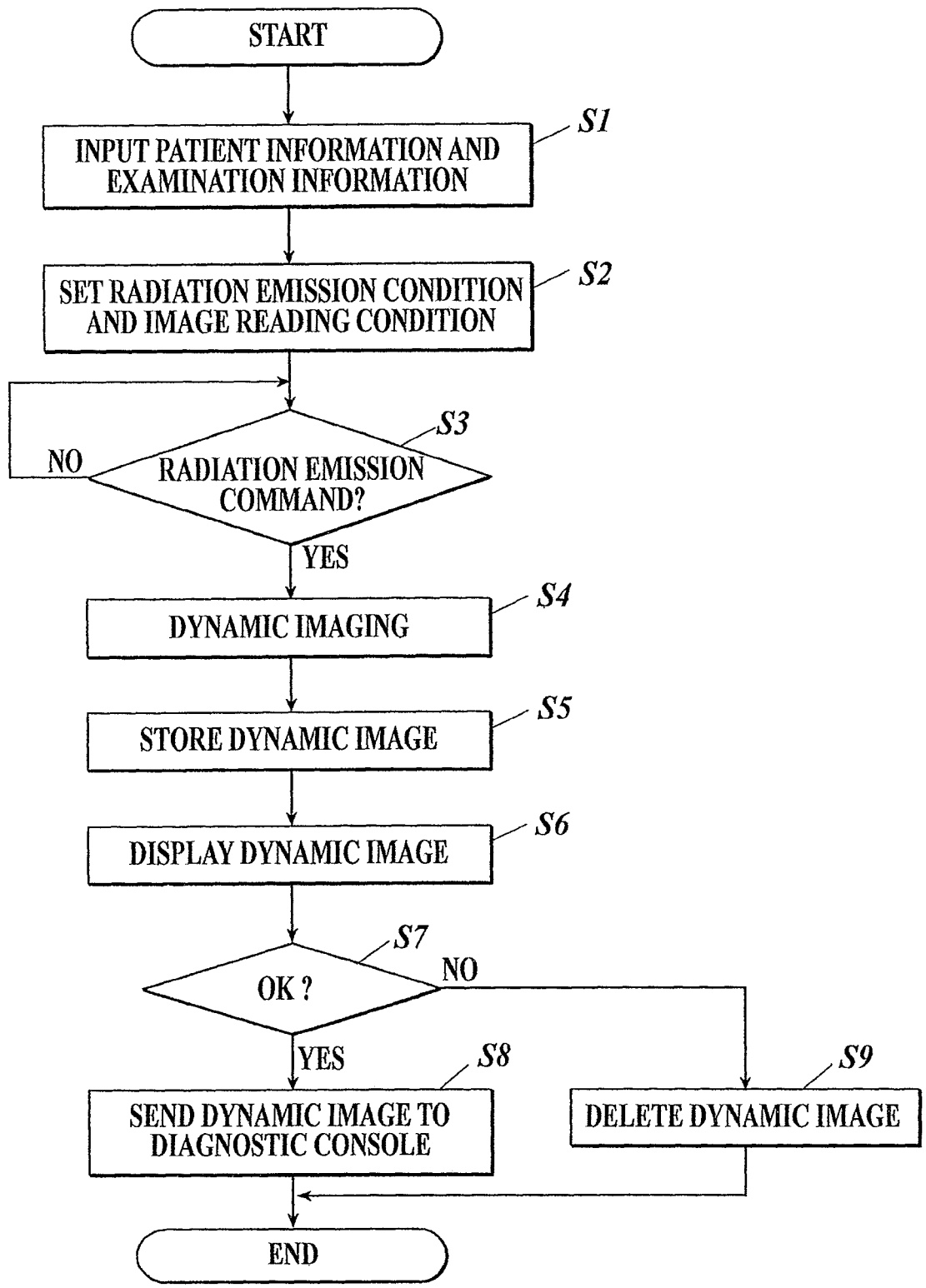
FIG. 2 is a flowchart of an imaging control process that is performed by a controller of an imaging console shown in FIG. 1.

FIG. 2 shows the imaging control process that is performed by the controller 21 of the imaging console 2. The imaging control process is performed by the controller 21 in cooperation with the program stored in the storage 22.

First, a radiographer operates the operation unit 23 of the imaging console 2 so as to input patient information on an examinee (subject M), and examination information on an examination to be performed on the examinee (Step S1).

Next, the controller 21 reads radiation emission conditions from the storage 22 so as to set them in the radiation emission controller 12, and also reads image reading conditions from the storage 22 so as to set them in the reading controller 14 (Step S2).

Next, the controller 21 waits for a radiation emission command to be input by the radiographer operating the operation unit 23 (Step S3). Here, the radiographer places the subject M between the radiation source 11 and the radiation detector 13 and performs positioning. Further, the radiographer instructs the examinee (subject M) about how to breathe, for example, instructs the examinee to relax and encourages him/her to do quiet breathing. If the type of the function to be diagnosed is ventilation, the radiographer may instruct the examinee to do quiet breathing, whereas if the type of the function to be diagnosed is perfusion, the radiographer may instruct the examinee to stop breathing. When preparations for imaging are complete, the radiographer operates the operation unit 23 so as to input the radiation emission command.

When receiving the radiation emission command input through the operation unit 23 (Step S3; YES), the controller 21 outputs an imaging start command to the radiation emission controller 12 and the reading controller 14 to start dynamic imaging (Step S4). That is, the radiation source 11 emits radiation at pulse intervals set in the radiation emission controller 12, and accordingly the radiation detector 13 obtains (generates) a series of frame images.

When imaging for a predetermined number of frame images finishes, the controller 21 outputs an imaging end command to the radiation emission controller 12 and the reading controller 14 to stop the imaging actions. The number of frame images to be taken covers at least one breathing cycle.

The frame images obtained by imaging are successively input to the imaging console 2 and stored in the storage 22, the frame images being correlated with respective numbers indicating what number in the imaging order the respective frame images have been taken (frame numbers) (Step S5), and also displayed on the display 24 (Step S6). The radiographer checks the positioning or the like with the displayed dynamic image, and determines whether the dynamic image obtained by dynamic imaging is suitable for diagnosis (Imaging OK) or re-imaging is necessary (Imaging NG). Then, the radiographer operates the operation unit 23 so as to input the determination result.

When the determination result "Imaging OK" is input by the radiographer performing a predetermined operation with the operation unit 23 (Step S7; YES), the controller 21 attaches, to the respective frame images of the dynamic image obtained by dynamic imaging (e.g. writes, in the header region of the image data in DICOM), information such as an ID to identify the dynamic image, the patient information, the examination information, the radiation emission conditions, the image reading conditions, and the respective numbers indicating what number in the imaging order the respective frame images have been taken (frame numbers), and sends the same to the diagnostic console 3 through the communication unit 25 (Step S8), and then ends the imaging control process. On the other hand, when the determination result "Imaging NG" is input by the radiographer performing a predetermined operation with the operation unit 23 (Step S7; NO), the controller 21 deletes the frame images of the dynamic image from the storage 22 (Step S9), and then ends the imaging control process. In this case, re-imaging is necessary.

[Actions of Diagnostic Console 3]

Next, actions of the diagnostic console 3 are described.

Figure 3:
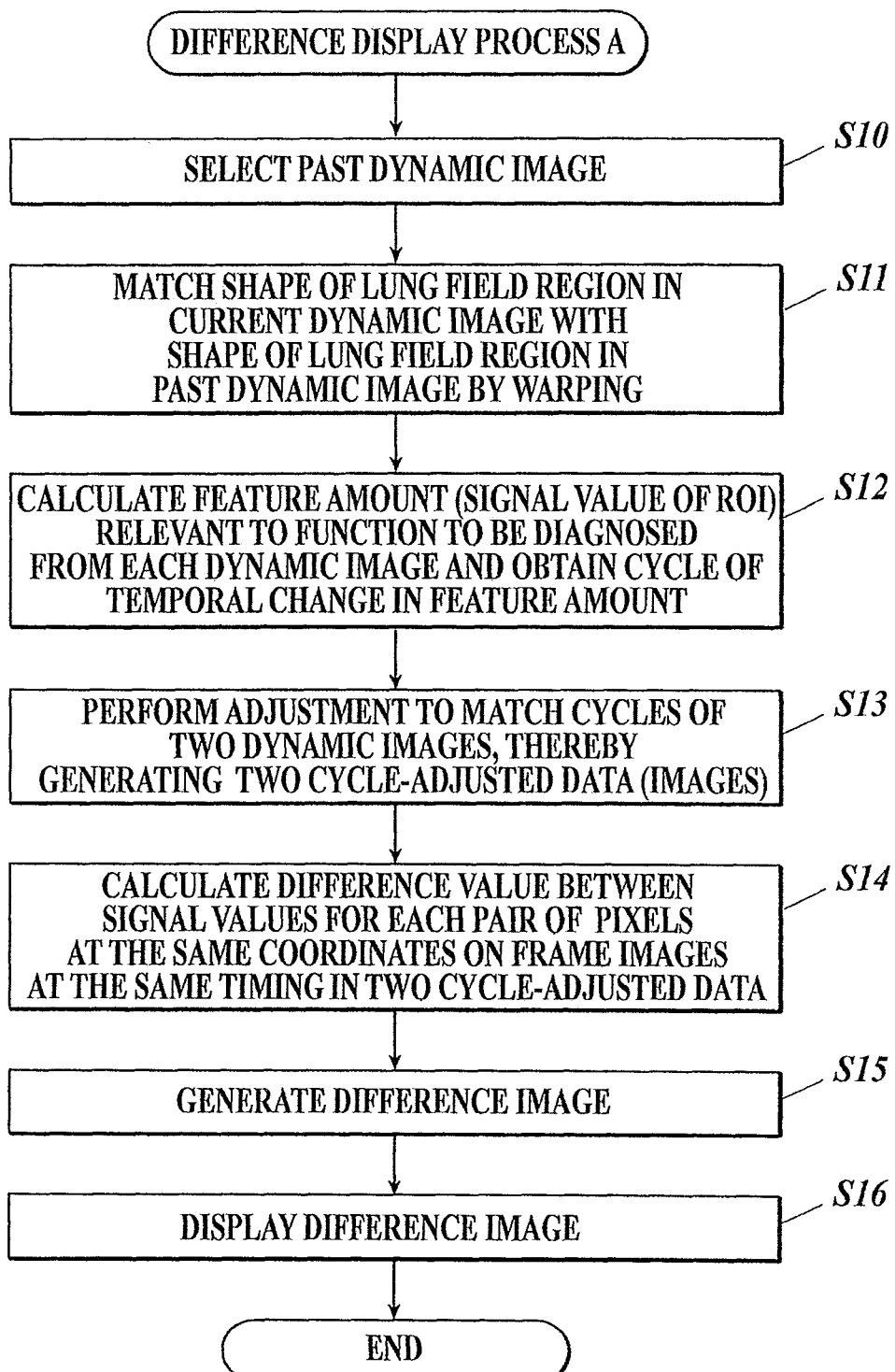
FIG. 3 is a flowchart of a difference display process A that is performed by a controller of a diagnostic console shown in FIG. 1 according to a first embodiment.

In the diagnostic console 3, when receiving a series of frame images of a dynamic image based on which ventilation or perfusion is diagnosed from the imaging console 2 through the communication unit 35, the controller 31 performs the difference display process A shown in FIG. 3 in cooperation with the program stored in the storage 32.

Hereinafter, the flow of the difference display process A is described with reference to FIG. 3.

First, a past dynamic image to be compared with the received dynamic image is selected (Step S10).

In Step S10, for example, a list of past dynamic images of the subject M stored in the storage 32 is displayed on the display 34, and from the displayed dynamic images, a dynamic image desired by a user is selected through the operation unit 33, or from the past dynamic images of the subject M stored in the storage 32, a dynamic image having the latest examination date is automatically selected by the controller 31. Note that the received dynamic image is referred to as a current dynamic image, and the dynamic image to be compared with the current dynamic image is referred to as a past dynamic image.

Next, the controller 31 performs warping on the current dynamic image and the past dynamic image so as to match the shapes of regions of lung fields (hereinafter "lung field region shapes") (Step S11).

For example, in Step S11, first, the contours of the lung field regions are detected from each frame image of the current dynamic image and each frame image of the past dynamic image. For example, for each frame image, a threshold value is obtained from a histogram of signal values (density values) of pixels by discriminant analysis, and regions having higher signal values than the threshold value are extracted as lung field region candidates. Then, edge detection is performed on around the border of each extracted lung field region candidate, and, in small regions around the border, points where the edge is the maximum are extracted along the border. Thus, the borders of the lung field regions can be extracted. Next, one frame image is selected from all the frame images of the current dynamic image and the past dynamic image as a reference image, and warping is performed such that the lung field region shapes in the other frame images match the lung field region shapes in the reference image. The reference image may be the first frame image of the current dynamic image or the past dynamic image, or may be a frame image at the maximal expiratory level or the maximal inspiratory level. Alternatively, an image of the lung field region shapes may be prepared beforehand as a reference, and the lung field region shapes in both dynamic images may be made to match the lung field region shapes serving as the reference. This makes the lung field region shapes always the same when dynamic images are compared with one another, and accordingly a user can compare and evaluate the dynamic images under the same environment.

Next, the controller 31 calculates the feature amount (here, signal value(s) of an ROI) relevant to the function to be diagnosed from each of the current dynamic image and the past dynamic image, and obtains cycles of temporal change in the calculated feature amount (Step S12).

As to the ventilation function by respiration, when the lung fields expand by inspiration, the density of the lung fields decreases, so that the X-ray transmission amount increases, and the signal values (density values) of the lung field regions in a dynamic image increases. On the other hand, when the lung fields contract by expiration, the density of the lung fields increases, so that the X-ray transmission amount decreases, and the signal values of the lung field regions in a dynamic image decreases. Hence, if the function to be diagnosed is ventilation, temporal change in signal value of a dynamic image can be used as temporal change in the feature amount relevant to the ventilation function. Further, when blood flows into the lung fields by respiration, the X-ray transmission amount at the parts where the blood flows decreases, and the signal values of the parts in a dynamic image decreases. Hence, if the function to be diagnosed is perfusion, temporal change in signal value of a dynamic image can be used as temporal change in the feature amount relevant to the perfusion function.

If the function to be diagnosed is, for example, ventilation, first, low-pass filtering in the time direction is performed on the lung field regions in both the past dynamic image and the current dynamic image. More specifically, for each pixel of each dynamic image, temporal change in signal value is obtained and filtered with a time-direction low-pass filter (e.g. a cutoff frequency of 0.80 Hz). This can remove the high-frequency component due to perfusion or the like and obtain the signal component due to ventilation.

Next, in each frame image of each of the two low-pass filtered dynamic images, an ROI (region of interest) is set. It is preferable that the ROI be set at a location where the feature relevant to the function to be diagnosed appears most clearly. If the function to be diagnosed is ventilation, it is preferable that the ROI be set in the lung field regions excluding the heart and backbones. The ROI may be set automatically by image processing or may be set in response to a user operation through the operation unit 33 (i.e. manually).

Next, for each of the current dynamic image and the past dynamic image, a representative value (e.g. the mean, the median, etc.) of the signal values of the pixels of the ROI in each frame image is calculated, and a graph of the waveform (called a waveform graph) showing temporal change in signal value (representative value) is generated by plotting the calculated representative values in chronological order (in order of the frame images).

Then, cycles of temporal change in signal value of the current dynamic image and the past dynamic image are obtained from the respective waveform graphs generated. Time from a local maximum point (or local minimum point) to the next local maximum point (or local minimum point) of the waveform graph(s) can be calculated as a cycle.

If the function to be diagnosed is, for example, perfusion, first, high-pass filtering in the time direction is performed on the lung field regions in both the past dynamic image and the current dynamic image. More specifically, for each pixel of each dynamic image, temporal change in signal value is obtained and filtered with a time-direction high-pass filter (e.g. a cutoff frequency of 0.80 Hz). The temporal change in signal value may be filtered with a time-direction bandpass filter (e.g. a lower-limit cutoff frequency of 0.8 Hz and an upper-limit cutoff frequency of 2.4 Hz). This can remove the low-frequency component due to ventilation or the like and obtain the signal component due to perfusion.

Next, in each frame image of each of the two filtered dynamic images, an ROI (region of interest) is set. It is preferable that the ROI be set at a location where the feature relevant to the function to be diagnosed appears most clearly. If the function to be diagnosed is perfusion, it is preferable that the ROI be set in the heart region. The ROI may be set automatically by image processing or may be set in response to a user operation through the operation unit 33 (i.e. manually).

Next, for each of the current dynamic image and the past dynamic image, a representative value (e.g. the mean, the median, etc.) of the signal values of the pixels of the ROI in each frame image is calculated, and a graph of the waveform (waveform graph) showing temporal change in signal value (representative value) is generated by plotting the calculated representative values in chronological order (in the order of the frame images).

Then, cycles of temporal change in signal value in the current dynamic image and the past dynamic image are obtained from the respective waveform graphs generated.

Next, the controller 31 performs cycle adjustment to match the cycles calculated from the current dynamic image with the cycles calculated from the past dynamic image, thereby generating two cycle-adjusted data (Step S13).

Figure 4:
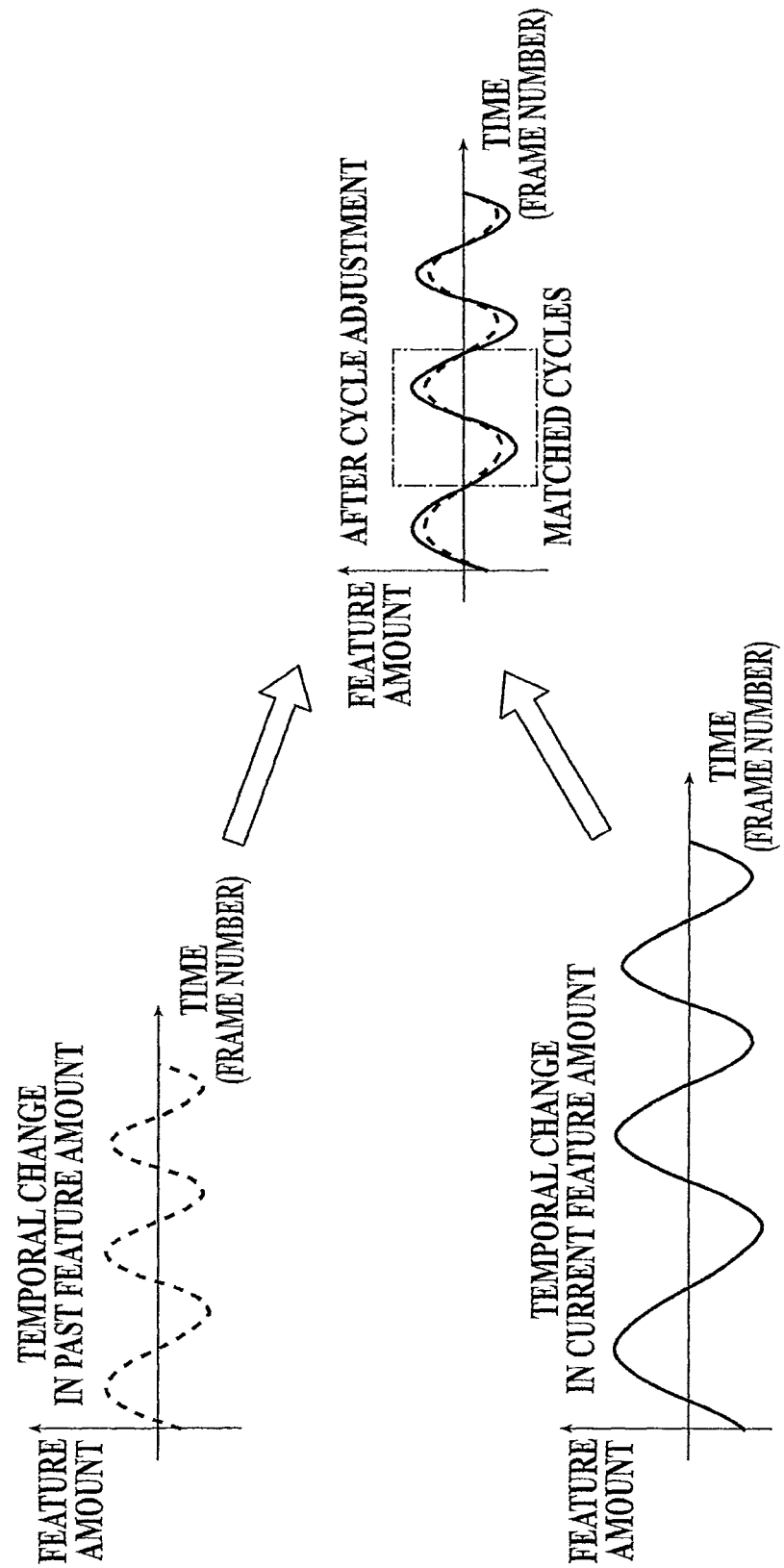
FIG. 4 is a diagram to explain cycle adjustment.

In Step S13, if the cycles obtained from the current dynamic image and the cycles obtained from the past dynamic image are different from one another as shown in FIG. 4, cycle adjustment is performed, so that two cycle-adjusted data, the cycles of which are equal to one another, are generated. In this embodiment, cycle-adjusted data are the dynamic images, the cycles of which have been matched with one another (here, the current dynamic image and the past dynamic image, the cycles of which have been matched with one another).

For example, first, cycles (cycles of temporal change in signal value; the same applies hereinafter) of the dynamic images after adjustment are determined. As the cycles after adjustment, shorter cycles that one of the dynamic images has may be used so that cycles of the other dynamic image are adjusted thereto, or longer cycles that one of the dynamic images has may be used so that cycles of the other dynamic image are adjusted thereto. Alternatively, cycles of both of the dynamic images may be adjusted to a predetermined cycle(s).

Next, in order to match the cycles of the respective dynamic images with the cycles after adjustment, for each cycle of each dynamic image, the number of frame images to be added or deleted is determined. If the number of frame images to be added or deleted is 0, the cycles of such a dynamic image are not changed. In each cycle of the dynamic image that needs cycle change, frame image(s) of the determined number are added or deleted, so that the cycles of the two dynamic images match. Thus, two dynamic images, the cycles of which are equal to one another, namely, two cycle-adjusted data, are generated.

For example, if shorter cycles are adjusted to longer cycles, frame images are evenly added to the dynamic image having shorter cycles, so that the cycles of the two dynamic images match. The signal values of the pixels of each frame image to be added can be obtained by interpolation, such as bilinear interpolation or bicubic interpolation, using, for example, signal values of pixels of a plurality of frame images of the original dynamic image, the pixels being at the same positions as the pixels of each frame image to be added. On the other hand, if longer cycles are adjusted to shorter cycles, frame images are evenly thinned out (deleted) from the dynamic image having longer cycles, so that the cycles of the two dynamic images match.

Alternatively, as the cycle-adjusted data, the dynamic images having cycles of temporal change in signal value being equal to one another may be generated by, in each cycle of the dynamic image(s) that needs cycle change, selecting a plurality of frame images, and generating an interpolation image(s) on the basis of the signal values of the selected frame images and the determined number of frame images. For example, the cycle-adjusted data may be generated by, for each group of corresponding pixels between the frame images of the dynamic image(s) that needs cycle change, generating a waveform graph showing temporal change in signal value and obtaining values at local maximum points and local minimum points, and generating an interpolation image(s) by bilinear interpolation, bicubic interpolation or the like on the basis of the number of frame images in each cycle after cycle adjustment and the obtained signal values at the local maximum points and the local minimum points, thereby adjusting the number of frame images in each cycle. This technique enables cycle adjustment even if the above addition/thinning-out is not usable (i.e. if frame images cannot be added/deleted evenly).

After cycle adjustment, shifting amounts in the time direction are calculated for the respective cycle-adjusted data to match their phases at the start timing in the two cycle-adjusted data with a predetermined phase (e.g. a local maximum point or a local minimum point), and the frame images of the cycle-adjusted data are shifted by their respective shifting amounts in the time direction. This can match the phases at the start timing in the two cycle-adjusted data.

Next, the controller 31 calculates, for each pair (or group) of pixels at the same coordinates on frame images at the same timing (each timing) in the two cycle-adjusted data, a difference value between the signal values (e.g. in this embodiment, a value obtained by subtracting the signal value of the past cycle-adjusted data from the signal value of the current cycle-adjusted data) (Step S14), and generates a difference image (Step S15).

In Step S15, the controller 31 generates the difference image, for example, by applying a color for the calculated difference value (a sign (+ or −) and the absolute value) to each pixel of one of the two cycle-adjusted data (e.g. the cycle-adjusted data of the past dynamic image).

The controller 31 then displays the generated difference image on the display 34 (Step S16) and ends the difference display process A.

FIG. 5 shows an example of the difference image at two different timings displayed in Step S16. As shown in FIG. 5, at the timing when the current signal values are higher than the past signal values, a color indicating increase in signal value is applied to each pixel with a density for the magnitude of the absolute value of the difference value. On the other hand, at the timing when the current signal values are lower than the past signal values, a color indicating decrease in signal value is applied to each pixel with a density for the magnitude of the absolute value of the difference value. Hence, a user can readily understand difference between the dynamic images, which are compared with one another, in the function to be diagnosed.

Modification from First Embodiment

Although two dynamic images obtained by imaging of the dynamic state of a subject are compared with one another in the first embodiment, the difference display process A is also applicable to the case where analysis result images are compared with one another, wherein each of the analysis result images is obtained by dynamic analysis of a dynamic image on a pixel-to-pixel basis (i.e. a pixel basis) or on a block-to-block basis (i.e. a block basis), the block being constituted of a plurality of pixels (e.g. the case where the controller 31 has a function to analyze dynamic images and generate analysis result images, and compares an analysis result image obtained by analysis of a current dynamic image with a past analysis result image of the same patient stored in the storage 32). That is, performing the same processes as those in Steps S11 to S16 of the difference display process A on two analysis result images that are compared with one another visualizes difference between the images and makes it easy for a user to understand the difference.

In this modification, warping in Step S11 is performed with the two dynamic images, based on which the two analysis result images have been generated. More specifically, warping is performed on the two dynamic images, based on which the two analysis result images have been generated, so as to match the lung field region shapes as described above, and the coordinate transform performed on the two dynamic images in the warping is also performed on the two analysis result images so as to match the lung field region shapes in the analysis result images.

Each analysis result image is obtained by analysis of a dynamic image on a pixel-to-pixel basis or on a block-to-block basis for the function (ventilation or perfusion) to be diagnosed, the block being constituted of a plurality of pixels, and the signal value(s) of the pixel(s) thereof is the feature amount relevant to the function to be diagnosed.

Although the specific analysis technique for obtaining analysis result images is not particularly limited, the (1) to (3) below can be used, for example. In the (1) to (3) below, analysis of a dynamic image is performed on a block-to-block basis, the block (small region) being constituted of a plurality of pixels, but may be performed on a pixel-to-pixel basis.

(1) If the function to be diagnosed is perfusion, the technique described in JP 2012-239796 A can be used, for example. That is, as a perfusion analysis result image, a moving image may be generated by calculating, for each small region of a series of frame images, a cross correlation coefficient of a pulsation signal waveform with a perfusion signal waveform while shifting the perfusion signal waveform by one frame interval (in the time direction) with respect to the pulsation signal waveform obtained from the start of imaging, and arranging images each being one frame in which the cross correlation coefficients are shown in the respective small regions, wherein the cross correlation coefficients for the respective small regions are calculated each time the perfusion signal waveform is shifted by one frame interval.

The perfusion signal waveform can be obtained by performing high-pass filtering in the time direction (e.g. a lower-limit cutoff frequency of 0.8 Hz) on each small region of a series of frame images, calculating a representative value (the mean, the maximum, etc.) of the signal values of the pixels of each small region, and obtaining a waveform showing temporal change in the calculated representative value.

As the pulsation signal waveform, any of the following waveforms can be used.
(a) Waveform that shows temporal change in signal value of ROI (region of interest) designated in heart region (or main artery region)
(b) Signal waveform obtained by reversing waveform of (a)
(c) Cardiac signal waveform obtained from electrocardiographic sensor
(d) Signal waveform that shows motion (change in position) of heart wall The cross correlation coefficient can be obtained by the following [Equation 1].

$$C = \frac{1}{J}\sum_{j=1}^{J} \frac{\{A(j) - m_A\}\{B(j) - m_B\}}{\sigma_A \sigma_B}$$ [Equation 1]

$$m_A = \frac{1}{J}\sum_{j=1}^{J} A(j), \quad m_B = \frac{1}{J}\sum_{j=1}^{J} B(j)$$

$$\sigma_A = \sqrt{\frac{1}{J}\sum_{j=1}^{J} \{A(j) - m_A\}^2}$$

$$\sigma_B = \sqrt{\frac{1}{J}\sum_{j=1}^{J} \{B(j) - m_B\}^2}$$

C: Cross correlation coefficient
$A(j)$: Signal value of $j^{th}$ signal of all signals J included in pulsation signal waveform
$m_A$: Mean of signal values of all signals included in pulsation signal waveform
$\sigma_A$: Standard deviation of all signals included in pulsation signal waveform $B(j)$: Signal value of $j^{th}$ signal of all signals J included in output signal waveform of small region
$m_B$: Mean of signal values of all signals included in output signal waveform of small region
$\sigma_B$: Standard deviation of all signals included in output signal waveform of small region (2) If the function to be diagnosed is perfusion, as described in JP 2013-81579 A, as a perfusion analysis result image, a moving image may be generated by performing high-pass filtering in the time direction (e.g. a lower-limit cutoff frequency of 0.8 Hz) on each small region of a series of frame images, calculating, for each small region, a difference value in representative value (the mean, the maximum, etc.) of the signal values of the pixels between adjacent frame images of each possible pair, and arranging images as frames in chronological order, each image being one frame in which the calculated difference values between the adjacent frame images are shown in the respective small regions. The inter-frame difference images (constituting the moving image) generated by the above technique are images from which signal change due to ventilation in each small region has been removed and which show signal change due to perfusion in each small region.

(3) If the function to be diagnosed is ventilation, as described in JP 2013-81579 A, as a ventilation analysis result image, a moving image may be generated by performing low-pass filtering in the time direction (e.g. a higher-limit cutoff frequency of 0.8 Hz) on each small region of a series of frame images, calculating, for each small region, a difference value in representative value (the mean, the maximum, etc.) of the signal values of the pixels between adjacent frame images of each possible pair, and arranging images as frames in chronological order, each image being one frame in which the calculated difference values between the adjacent frame images are shown in the respective small regions. The inter-frame difference images (constituting the moving image) generated by the above technique are images from which signal change due to perfusion in each small region has been removed and which show signal change due to ventilation in each small region.

Second Embodiment

Next, a second embodiment of the invention is described.

The configuration of the second embodiment is the same as that described in the first embodiment except that, in the second embodiment, a program to perform a difference display process B is stored in the storage 32 of the diagnostic console 3. Hence, description of the configuration is not repeated here, and actions of the second embodiment are described hereinafter.

First, the imager 1 and the imaging console 2 perform dynamic imaging, thereby generating a dynamic image, and the imaging console 2 sends a series of frame images of the dynamic image to the diagnostic console 3.

Figure 6:
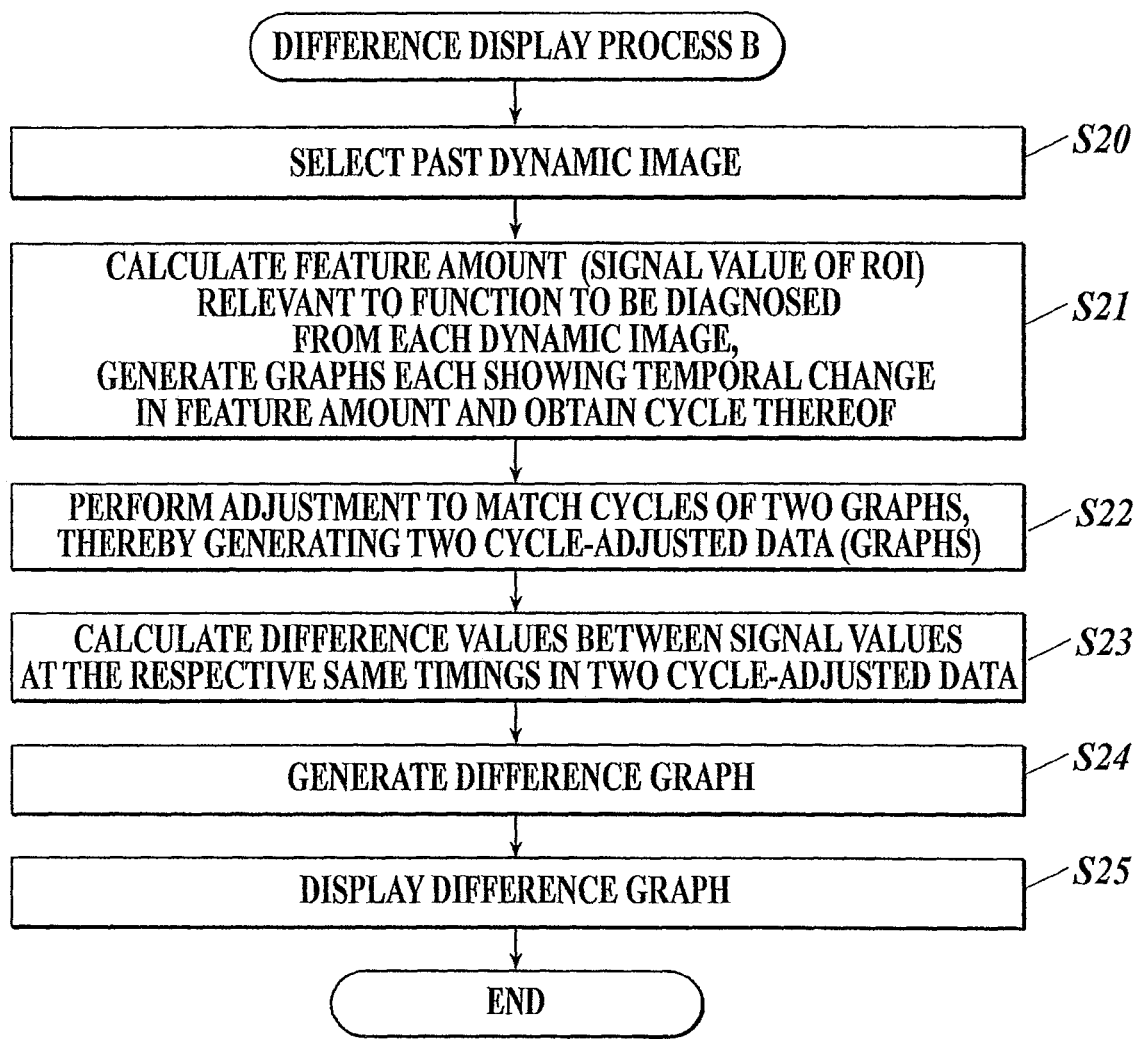
FIG. 6 is a flowchart of a difference display process B that is performed by the controller of the diagnostic console shown in FIG. 1 according to a second embodiment.

In the diagnostic console 3, when receiving the series of frame images of the dynamic image based on which ventilation or perfusion is diagnosed from the imaging console 2 through the communication unit 35, the controller 31 performs the difference display process B shown in FIG. 6 in corporation with the program stored in the storage 32.

FIG. 6 is a flowchart of the difference display process B that is performed by the diagnostic console 3 in the second embodiment. The difference display process B is performed by the controller 31 in cooperation with the program stored in the storage 32.

Hereinafter, the flow of the difference display process B is described with reference to FIG. 6.

First, a past dynamic image to be compared with the received dynamic image is selected (Step S20).

The process in Step S20 is the same as that in Step S10 shown in FIG. 3, and hence description thereof is not repeated here.

Next, the controller 31 calculates the feature amount (here, signal value(s) of an ROI) relevant to the function to be diagnosed from each of the current dynamic image and the past dynamic image, generates waveform graphs each showing temporal change in the calculated feature amount and obtains cycles thereof (Step S21).

The process in Step 21 is the same as that in Step S12 shown in FIG. 3, and hence description thereof is not repeated here. Note that each data plotted on each waveform graph is called signal value data.

Next, the controller 31 performs cycle adjustment to match the cycles of the waveform graph generated on the basis of the current dynamic image with the cycles of the waveform graph generated on the basis of the past dynamic image, thereby generating two cycle-adjusted data (Step S22).

In Step S22, if the cycles of the waveform graph generated on the basis of the current dynamic image and the cycles of the waveform graph generated on the basis of the past dynamic image are different from one another as shown in FIG. 4, cycle adjustment is performed, so that their cycles become equal to one another. In this embodiment, the cycle-adjusted data are the waveform graphs, the cycles of which have been matched with one another.

For example, first, cycles (cycles of temporal change in signal value; the same applies hereinafter) of the waveform graphs after adjustment are determined. As the cycles after adjustment, shorter cycles that one of the dynamic images has may be used so that cycles of the other dynamic image are adjusted thereto, or longer cycles that one of the dynamic images has may be used so that cycles of the other dynamic image are adjusted thereto. Alternatively, cycles of both of the dynamic images may be adjusted to a predetermined cycle(s).

Next, in order to match the cycles of the respective waveform graphs with the cycles after adjustment, for each cycle of each waveform graph, the number of signal value data to be added or deleted is determined. If the number of signal value data to be added or deleted is 0, the cycles of such a waveform graph are not changed. In each cycle of the waveform graph that needs cycle change, signal value data of the determined number are added or deleted, so that the cycles of the two waveform graphs match. Thus, two waveform graphs, the cycles of which are equal to one another, namely, two cycle-adjusted data, are generated.

For example, if shorter cycles are adjusted to longer cycles, signal value data are evenly added to the waveform graph having shorter cycles, so that the cycles of the two waveform graphs match. The signal value data to be added can be obtained by interpolation, such as bilinear interpolation or bicubic interpolation, using, for example, signal value data of the original waveform graph. On the other hand, if longer cycles are adjusted to shorter cycles, signal value data are evenly thinned out (deleted) from the waveform graph having longer cycles, so that the cycles of the two waveform graphs match. The interval to plot signal value data on the waveform graphs is the frame interval in imaging.

Alternatively, a waveform graph(s) having cycles that are the determined cycles may be newly generated by, in each cycle of the waveform graph(s) that needs cycle change, selecting a plurality of signal value data (e.g. a local maximum point and a local minimum point), and performing interpolation on the basis of the selected signal value data and the cycles of the waveform graphs after adjustment. For example, the cycle-adjusted data may be generated by, from the waveform graph(s) that needs cycle change, obtaining local maximum points and local minimum points of signal value data, and interpolating signal value data by bilinear interpolation, bicubic interpolation or the like on the basis of the cycles after adjustment and the signal value data of the obtained local maximum points and local minimum points, thereby adjusting the cycles of the waveform graph(s). This technique enables cycle adjustment even if the above addition/thinning-out is not usable (i.e. if signal value data cannot be added/deleted evenly).

After cycle adjustment, shifting amounts in the time direction are calculated for the respective cycle-adjusted data to match their phases at the start timing in the two cycle-adjusted data with a predetermined phase (e.g. a local maximum point or a local minimum point), and the signal value data of the cycle-adjusted data are shifted by their respective shifting amounts in the time direction. This can match the phases at the start timing in the two cycle-adjusted data.

Next, the controller 31 calculates difference values between the signal values at the respective same timings in the two cycle-adjusted data (e.g. values obtained by subtracting the signal value data of the cycle-adjusted data of the waveform graph generated on the basis of the past dynamic image (past cycle-adjusted data) from their corresponding signal value data of the cycle-adjusted data of the waveform graph generated on the basis of the current dynamic image (current cycle-adjusted data)) (Step S23), and generates a difference graph (Step S24).

In Step S24, the controller 31 generates the difference graph, for example, by integrating the two cycle-adjusted data (graphs) into one, adding a waveform of the difference values onto the graph, and applying colors for the difference values to the waveform of the difference values.

The controller 31 then displays the generated difference graph on the display 34 (Step S25) and ends the difference display process B.

Figure 7:
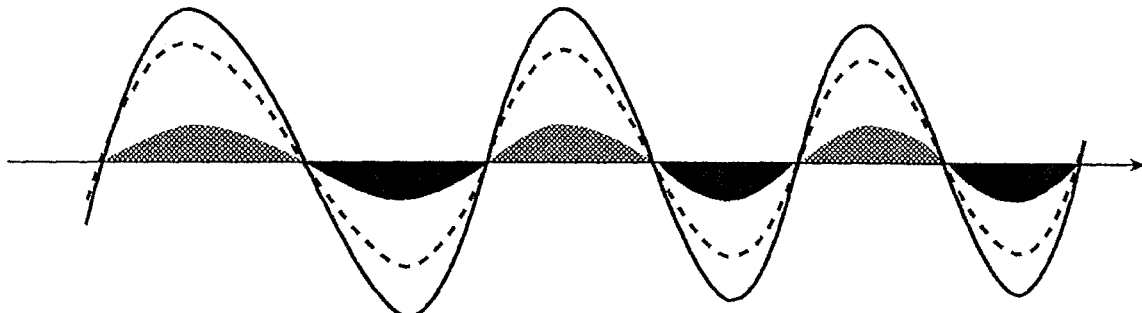
FIG. 7 shows a difference graph displayed in Step S25 in FIG. 6.

FIG. 7 shows an example of the difference graph displayed in Step S25. As shown in FIG. 7, in the difference graph, the waveforms showing temporal change in the feature amount in the two dynamic images, namely, the past dynamic image and the current dynamic image, and the waveform showing difference therebetween are superimposed and displayed. At the timings when the current signal values are higher than the past signal values, a color indicating increase in signal value is applied to the waveform showing the difference. On the other hand, at the timings when the current signal values are lower than the past signal values, a color indicating decrease in signal value is applied to the waveform showing the difference. Hence, a user can readily understand difference between the dynamic images, which are compared with one another, in the function to be diagnosed.

Modification from Second Embodiment

Although two dynamic images obtained by imaging of the dynamic state of a subject are compared with one another in the second embodiment, the difference display process B is also applicable to the case where analysis result images are compared with one another, wherein each of the analysis result images is obtained by dynamic analysis of a dynamic image on a pixel-to-pixel basis or on a block-to-block basis, the block being constituted of a plurality of pixels (e.g. the case where the controller 31 has a function to analyze dynamic images and generate analysis result images, and compares an analysis result image obtained by analysis of a current dynamic image with a past analysis result image of the same patient stored in the storage 32). That is, performing the same processes as those in Steps S21 to S25 of the difference display process B on two analysis result images that are compared with one another visualizes difference between the images and makes it easy for a user to understand the difference.

Examples of the analysis result images are the same as those described in the first embodiment. Hence, description thereof is not repeated here.

Third Embodiment

Next, a third embodiment of the invention is described.

The configuration of the third embodiment is the same as that described in the first embodiment except that, in the third embodiment, a program to perform a difference display process C is stored in the storage 32 of the diagnostic console 3. Hence, description of the configuration is not repeated here, and actions of the third embodiment are described hereinafter.

First, the imager 1 and the imaging console 2 perform dynamic imaging, thereby generating a dynamic image, and the imaging console 2 sends a series of frame images of the dynamic image to the diagnostic console 3.

Figure 8:
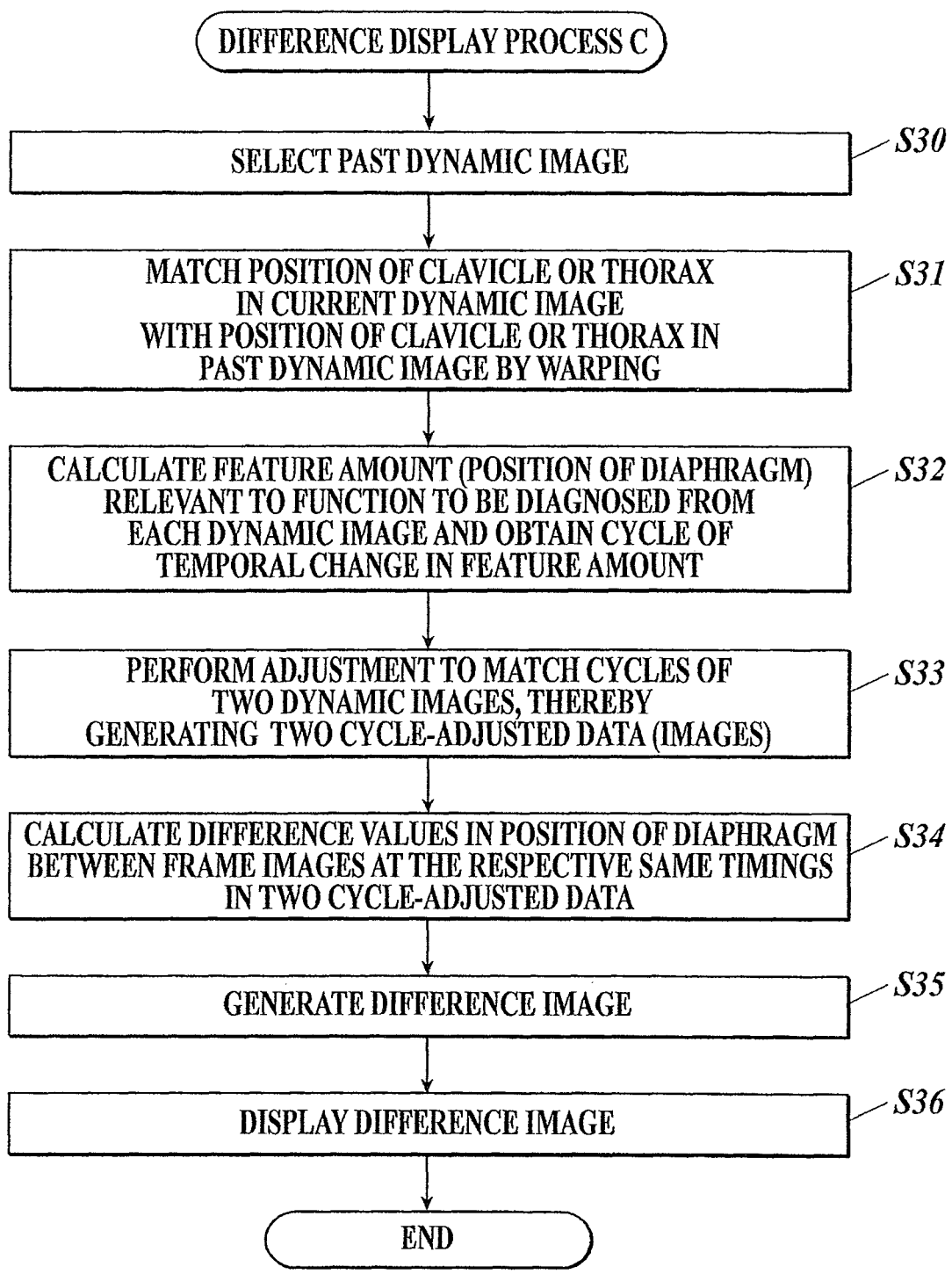
FIG. 8 is a flowchart of a difference display process C that is performed by the controller of the diagnostic console shown in FIG. 1 according to a third embodiment.

In the diagnostic console 3, when receiving the series of frame images of the dynamic image based on which the function of the diaphragm is diagnosed from the imaging console 2 through the communication unit 35, the controller 31 performs the difference display process C shown in FIG. 8 in corporation with the program stored in the storage 32.

FIG. 8 is a flowchart of the difference display process C that is performed by the diagnostic console 3 in the third embodiment. The difference display process C is performed by the controller 31 in cooperation with the program stored in the storage 32.

Hereinafter, the flow of the difference display process C is described with reference to FIG. 8.

First, a past dynamic image to be compared with the received dynamic image is selected (Step S30).

The process in Step S30 is the same as that in Step S10 shown in FIG. 3, and hence description thereof is not repeated here.

Next, the controller 31 performs warping on the current dynamic image and the past dynamic image so as to perform position adjustment of the clavicle or the thorax (Step S31).

For example, in Step S31, first, the clavicle or the thorax is extracted in each frame image of the current dynamic image and each frame image of the past dynamic image. The clavicle or the thorax can be extracted, for example, by template matching on each frame image using a prepared template, such as a clavicle template, a rib template or a sternum temperate, or by application of curve fitting function to each frame image after edge detection. Further, on the basis of features, such as the position, shape, size, concentration gradient and direction, based on previous knowledge of bone structures of the clavicle and/or the thorax, whether or not the extracted region(s) is the clavicle or the thorax may be carefully examined so that excessively extracted parts can be distinguished and removed. Next, one frame image is selected from all the frame images of the current dynamic image and the past dynamic image as a reference image, and warping is performed such that the position of the clavicle or the thorax in the other frame images matches the position of the clavicle or the thorax in the reference image. The reference image may be the first frame image of the current dynamic image or the past dynamic image, or may be a frame image at the maximal expiratory level or the maximal inspiratory level.

Next, the controller 31 calculates the feature amount (here, the position of the diaphragm (i.e. the diaphragm position)) relevant to the function to be diagnosed from each of the current dynamic image and the past dynamic image, and obtains cycles of temporal change in the calculated feature amount (Step S32).

In Step S32, first, the diaphragm position in each frame image of the current dynamic image and the past dynamic image is identified. In a plain chest roentgenogram taken from the front, the diaphragm appears to be in contact with the bottom of the lung fields. Hence, for example, the lung field regions are extracted in each frame image, and the contours at the bottom of the extracted lung field regions can be identified as the diaphragm position.

Next, for each of the current dynamic image and the past dynamic image, a representative value (e.g. the mean, the median, etc.) of y coordinates of the diaphragm position identified in each frame image is calculated, and a graph of the waveform (called a waveform graph) showing temporal change in diaphragm position is generated by plotting the calculated representative values in chronological order (in order of the frame images). The horizontal direction and the vertical direction of each image are the x direction and the y direction, respectively. In addition, the upper left of each image is the origin, and the y coordinate value is larger on the lower side in the y direction.

Then, cycles of temporal change in diaphragm position in the current dynamic image and the past dynamic image are obtained from the respective waveform graphs generated. Time from a local maximum point (or local minimum point) to the next local maximum point (or local minimum point) of the waveform graph(s) showing temporal change in diaphragm position can be calculated as a cycle.

Next, the controller 31 performs cycle adjustment to match the cycles obtained from the current dynamic image with the cycles obtained from the past dynamic image, thereby generating two cycle-adjusted data (Step S33).

In Step S33, if the cycles obtained from the current dynamic image and the cycles obtained from the past dynamic image are different from one another as shown in FIG. 4, cycle adjustment is performed, so that two cycle-adjusted data, the cycles of which are equal to one another, are generated. In this embodiment, cycle-adjusted data are the dynamic images, the cycles of which have been matched with one another (here, the current dynamic image and the past dynamic image, the cycles of which have been matched with one another).

For example, first, cycles (cycles of temporal change in diaphragm position; the same applies hereinafter) of the dynamic images after adjustment are determined. As the cycles after adjustment, shorter cycles that one of the dynamic images has may be used so that cycles of the other dynamic image are adjusted thereto, or longer cycles that one of the dynamic images has may be used so that cycles of the other dynamic image are adjusted thereto. Alternatively, cycles of both of the dynamic images may be adjusted to a predetermined cycle(s).

Next, in order to match the cycles of the respective dynamic images with the cycles after adjustment, for each cycle of each dynamic image, the number of frame images to be added or deleted is determined. If the number of frame images to be added or deleted is 0, the cycles of such a dynamic image are not changed. In each cycle of the dynamic image that needs cycle change, frame image(s) of the determined number are added or deleted, so that cycles of the two dynamic images match. Thus, two dynamic images, the cycles of which are equal to one another, namely, two cycle-adjusted data, are generated.

For example, if shorter cycles are adjusted to longer cycles, frame images are evenly added to the dynamic image having shorter cycles, so that the cycles of the two dynamic images match. The signal values of the pixels of each frame image to be added can be obtained by interpolation, such as bilinear interpolation or bicubic interpolation, using, for example, signal values of a plurality of frame images of the original dynamic image. On the other hand, if longer cycles are adjusted to shorter cycles, frame images are evenly thinned out (deleted) from the dynamic image having longer cycles, so that the cycles of the two dynamic images match.

Alternatively, as the cycle-adjusted data, the dynamic images having cycles of temporal change in diaphragm position being equal to one another may be generated by, in each cycle of the dynamic image(s) that needs cycle change, selecting a plurality of frame images (e.g. images corresponding to a local maximum point and a local minimum point of the waveform graph(s) showing temporal change in the diaphragm position), and generating an interpolation image(s) by interpolation, such as bilinear interpolation or bicubic interpolation, on the basis of the selected frame images and the determined number of frame images. This technique enables cycle adjustment even if the above addition/thinning-out is not usable (i.e. if frame images cannot be added/deleted evenly).

After cycle adjustment, shifting amounts in the time direction are calculated for the respective cycle-adjusted data to match their phases at the start timing in the two cycle-adjusted data with a predetermined phase (e.g. a local maximum point or a local minimum point) of temporal change in diaphragm position, and the signal values of the cycle-adjusted data are shifted by their respective shifting amounts in the time direction. This can match the phases at the start timing in the two cycle-adjusted data.

Next, the controller 31 calculates difference values in the diaphragm position between frame images at the respective same timings in the two cycle-adjusted data (Step S34). More specifically, the controller 31 calculates a difference value in the vertical direction between the diaphragm position in each frame image of the current cycle-adjusted data and the diaphragm position in each frame image of the past cycle-adjusted data, the frame images being at the same timing.

Next, the controller 31 generates, on the basis of the obtained difference information, a difference image in which the difference information is superimposed on each frame image of one of the two cycle-adjusted data (Step S35).

In Step S35, the controller 31 generates the difference image, for example, by applying different colors to the current diaphragm position, the past diaphragm position and a region therebetween (difference region) in each frame image of one of the two cycle-adjusted data (e.g. the cycle-adjusted data of the past dynamic image). To the difference region, a color for a sign (+ or −) of the difference value is applied, for example.

The controller 31 then displays the generated difference image on the display 34 (Step S36) and ends the difference display process C.

Figure 9:
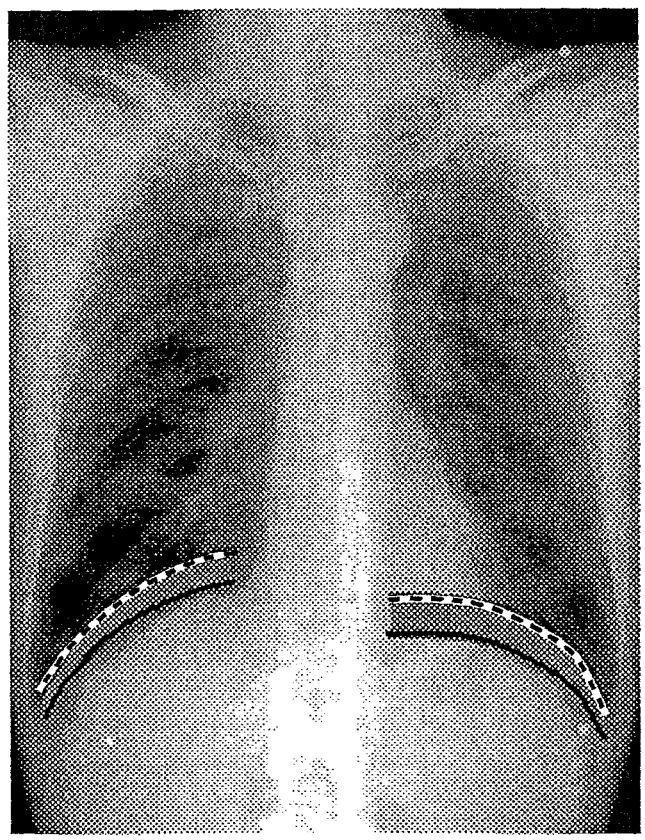
FIG. 9 shows a difference image (moving image) displayed in Step S36 in FIG. 8.

FIG. 9 shows an example of the difference image displayed in Step S36. As shown in FIG. 9, at the timing when the current diaphragm position is higher than the past diaphragm position (the difference value is positive (+)), a color indicating that the current diaphragm position is higher than the past diaphragm position is applied to the difference region between the current diaphragm position and the past diaphragm position. On the other hand, at the timing when the current diaphragm position is lower than the past diaphragm position (the difference value is negative (−)), a color indicating that the current diaphragm position is lower than the past diaphragm position is applied to the difference region between the current diaphragm position and the past diaphragm position. Hence, a user can readily understand difference between the dynamic images, which are compared with one another.

In the above, the first to third embodiments are described. However, the matters described in the above embodiments are some of preferred examples of the invention, and not intended to limit the invention.

For example, although the phases of the two cycle-adjusted data at the start timing are adjusted by shifting at least one of the cycle-adjusted data in the time direction in relation to one another in the above first embodiment and modification therefrom, this phase adjustment on the two cycle-adjusted data may be performed on a pixel-to-pixel basis. For example, as to perfusion in the lung fields, there may be phase lag between phases of temporal change in signal value near the heart and phases of temporal change in signal value at the distil end. If the phases about all the pixels of at least one of the cycle-adjusted data are uniformly shifted as described in the above first embodiment and modification therefrom, the phase lag due to the positions of the pixels remains, so that a user can understand the phase lag due to the positions of the pixels of the dynamic image(s) (analysis result image(s)). On the other hand, if shifting amounts in the time direction are determined for the respective pixels of the two cycle-adjusted data, the pixels of one cycle-adjusted data respectively corresponding to the pixels of the other cycle-adjusted data, and phase adjustment is performed such that phases about all the pixels are matched with one another, a user can readily judge difference in the magnitude of the difference value at each phase due to the positions of the pixels.

Further, if the type of the function to be diagnosed is the function of the diaphragm, a difference graph of waveform graphs showing temporal change in diaphragm position in two dynamic images that are compared with one another may be generated and displayed on the display 34. The difference graph of the waveform graphs of the diaphragm position can be generated by calculating the waveform graphs of the diaphragm position in Step S21 of the difference display process B shown in FIG. 6 using the technique described in Step S32 in FIG. 8, and performing the same processes as those in Steps S22 to S24 on the generated waveform graphs. In these steps, the "cycles" are replaced by the "cycles of temporal change in diaphragm position", and the "signal value data" are replaced by "diaphragm position data". The diaphragm position data each indicates data of the value of the diaphragm position plotted on each waveform graph of the diaphragm position.

Further, in the above embodiments, cycle-adjusted data based on two dynamic images or two analysis result images that are compared with one another are generated. However, the number of dynamic images or analysis result images that are compared with one another is not limited to two and may be more than two.

Further, although the display 34 is used as an output device in the above embodiments, another output device, such as a printer, may be used.

Further, although generation of the difference information (difference image or difference graph) from the dynamic images or the analysis result images and display of the generated difference information are both performed by a single apparatus in the above embodiments, these processes may be performed by different apparatuses. For example, generation of the difference information (difference image or difference graph) from the dynamic images or the analysis result images may be performed by an apparatus, and display of the generated difference information may be performed by another apparatus.

Further, in the above embodiments, the difference image is generated in the first embodiment and the third embodiments, and the difference graph is generated in the second embodiment. However, the diagnostic console 3 may have a function to generate both of the difference image and the difference graph, and be configured such that a user can choose one of them to be generated and displayed with the operation unit 33.

Further, for example, in the above, as a computer readable medium for the programs of the invention, a hard disk, a nonvolatile semiconductor memory or the like is used. However, the computer readable medium is not limited thereto, and may be a portable recording/storage medium, such as a CD-ROM. Further, as a medium to provide data of the programs of the invention, a carrier wave can be used.

In addition to the above, the specific configurations/components and the specific actions of the apparatuses of the dynamic analysis system can also be appropriately modified without departing from the spirit of the invention.

Although embodiments of the invention have been described and illustrated in detail, the disclosed embodiments are made for purposes of illustration and example only and not limitation. The scope of the invention should be interpreted by terms of the appended claims.

What is claimed is:

1. A dynamic analysis system comprising:
    a hardware processor that:
        analyzes a first dynamic image obtained by imaging of a dynamic state of a living body with radiation and generates a first analysis result image, and analyzes a second dynamic image obtained by imaging of the dynamic state of the living body with radiation and generates a second analysis result image; and
        generates difference information at each phase in the first analysis result image and the second analysis result image; and
    an output device that outputs the difference information.

2. The dynamic analysis system according to claim 1, wherein the hardware processor:
    obtains a cycle of temporal change in a first feature amount relevant to a function to be diagnosed from the first analysis result image and a cycle of temporal change in a second feature amount relevant to the function to be diagnosed from the second analysis result image; and
    adjusts the cycles obtained, thereby generating the first analysis result image and the second analysis result image having the cycles of the temporal change in the first feature amount and the second feature amount, respectively, the cycles being equal to one another.

3. The dynamic analysis system according to claim 2, wherein the hardware processor adds or deletes a frame image to or from at least one of the first analysis result image and the second analysis result image, thereby generating the first analysis result image and the second analysis result image having the cycles of the temporal change in the first feature amount and the second feature amount, respectively, the cycles being equal to one another.

4. The dynamic analysis system according to claim 3, wherein the hardware processor calculates signal values of pixels of the frame image to be added to the at least one of the first analysis result image and the second analysis result image by interpolation using signal values of pixels of a plurality of frame images of the at least one of the first analysis result image and the second analysis result image, to which the frame image is to be added, the pixels being at same positions as the pixels of the frame image to be added.

5. The dynamic analysis system according to claim 3, wherein the hardware processor:
    generates the first analysis result image and the second analysis result image having phases at a start timing being matched with one another; and
    calculates a difference value between signal values of pixels at same coordinates on frame images at a same timing in the first analysis result image and the second analysis result image.

6. The dynamic analysis system according to claim 2, wherein the hardware processor generates an interpolation image based on signal values of a plurality of frame images selected from frame images of at least one of the first analysis result image and the second analysis result image, thereby generating the first analysis result image and the second analysis result image having the cycles of the temporal change in the first feature amount and the second feature amount, respectively, the cycles being equal to one another.

7. The dynamic analysis system according to claim 2, wherein the hardware processor:
    generates a graph showing the temporal change in the first feature amount relevant to the function to be diagnosed from the first analysis result image and a graph showing the temporal change in the second feature amount relevant to the function to be diagnosed from the second analysis result image;
    obtains the cycle of the temporal change in the first feature amount and the cycle of the temporal change in the second feature amount based on the respective generated graphs; and
    changes at least one of the cycle of the graph showing the temporal change in the first feature amount generated from the first analysis result image and the cycle of the graph showing the temporal change in the second feature amount generated from the second analysis result image, thereby generating the graphs having the cycles of the temporal change in the first feature amount and the second feature amount, respectively, the cycles being equal to one another.

8. The dynamic analysis system according to claim 7, wherein the hardware processor:
    generates the first analysis result image and the second analysis result image having phases at a start timing being matched with one another; and
    calculates a difference value between signal values at a same timing in the first analysis result image and the second analysis result image.

9. The dynamic analysis system according to claim 2, wherein
    the function to be diagnosed is a perfusion function or a ventilation function in a lung field, and the first feature amount and the second feature amount are each a signal value of a pixel in a region of interest.

10. The dynamic analysis system according to claim 2, wherein
the function to be diagnosed is a function of a diaphragm, and
the first feature amount and the second feature amount are each a diaphragm position.

11. The dynamic analysis system according to claim 1, wherein the hardware processor combines the difference information with at least one of the first analysis result image and the second analysis result image, and causes the output device to output the difference information combined with the at least one of the first analysis result image and the second analysis result image.

12. The dynamic analysis system according to claim 1, wherein the first dynamic image and the second dynamic image are dynamic chest images.

13. A non-transitory computer readable storage medium storing a program that causes a computer to:
analyze a first dynamic image obtained by imaging of a dynamic state of a living body with radiation and generate a first analysis result image, and analyze a second dynamic image obtained by imaging of the dynamic state of the living body with radiation and generate a second analysis result image;
generate difference information at each phase in the first analysis result image and the second analysis result image; and
cause an output device to output the difference information.

14. The non-transitory computer readable storage medium according to claim 13, wherein the program further causes the computer to:
obtain a cycle of temporal change in a first feature amount relevant to a function to be diagnosed from the first analysis result image and a cycle of temporal change in a second feature amount relevant to the function to be diagnosed from the second analysis result image; and
adjust the cycles obtained, thereby generating the first analysis result image and the second analysis result image having the cycles of the temporal change in the first feature amount and the second feature amount, respectively, being equal to one another.

15. The non-transitory computer readable storage medium according to claim 14, wherein
the function to be diagnosed is a perfusion function or a ventilation function in a lung field, and
the first feature amount and the second feature amount are each a signal value of a pixel in a region of interest.

16. The non-transitory computer readable storage medium according to claim 14, wherein
the function to be diagnosed is a function of a diaphragm, and
the first feature amount and the second feature amount are each a diaphragm position.

17. The non-transitory computer readable storage medium according to claim 14, wherein the program further causes the computer to:
combine the difference information with at least one of the first analysis result image and the second analysis result image, and cause the output device to output the difference information combined with the at least one of the first analysis result image and the second analysis result image.

18. The non-transitory computer readable storage medium according to claim 13, wherein the first dynamic image and the second dynamic image are dynamic chest images.

19. A dynamic analysis method comprising:
analyzing a first dynamic image obtained by imaging of a dynamic state of a living body with radiation and generating a first analysis result image, and analyzing a second dynamic image obtained by imaging of the dynamic state of the living body with radiation and generating a second analysis result image; and
generating difference information at each phase in the first analysis result image and the second analysis result image; and
causing an output device to output the difference information.

20. The dynamic analysis method according to claim 19, wherein the first dynamic image and the second dynamic image are dynamic chest images.

* * * * *